(12) United States Patent  (10) Patent No.: US 6,575,749 B1
Greenwald  (45) Date of Patent: Jun. 10, 2003

(54) GINGIVAL RETRACTOR

(76) Inventor: Paul D. Greenwald, 1845 Autumn Leaf La., Huntingdon Valley, PA (US) 19006

( * ) Notice: Subject to any disclaimer, the term of this patent is extended or adjusted under 35 U.S.C. 154(b) by 0 days.

(21) Appl. No.: 10/119,732

(22) Filed: Apr. 11, 2002

(51) Int. Cl.$^7$ .................................................. A61L 9/00
(52) U.S. Cl. ...................................... 433/141; 600/237
(58) Field of Search ................................. 433/140, 141, 433/143, 144, 148; 600/210, 237

(56) References Cited

U.S. PATENT DOCUMENTS

| | | | | |
|---|---|---|---|---|
| 1,109,924 A | * | 9/1914 | Hoffman et al. | |
| 1,261,339 A | * | 4/1918 | Angle | |
| 1,497,749 A | * | 6/1924 | Diack | |
| 1,691,786 A | * | 11/1928 | Roth | |
| 2,835,972 A | * | 5/1958 | Sheldon | |
| 4,004,345 A | * | 1/1977 | Ely | |
| 4,854,867 A | | 8/1989 | Meinershagen | 433/40 |
| 5,004,419 A | * | 4/1991 | Kline | 433/143 |
| 5,039,302 A | * | 8/1991 | Keys | 433/3 |
| 5,378,151 A | * | 1/1995 | Lukase et al. | 433/150 |
| 6,024,564 A | * | 2/2000 | Kesling | 433/72 |
| 6,482,152 B2 | * | 11/2002 | Kim | 600/210 |

* cited by examiner

Primary Examiner—Ralph A. Lewis
(74) Attorney, Agent, or Firm—Gregory J. Gore

(57) ABSTRACT

A dental tool composed of molded plastic for gingival retraction includes an elongate handle and a horseshoe-shaped guard at an operative end of the handle. The guard includes a pair of downward extending elongate legs and a curved neck interconnects the handle and the guard. A wedge extends rearwardly from a top portion of the guard such that the legs of the guard lie along the surface of a tooth when the wedge is inserted between the gingiva and the root of the tooth at the gingival margin. The gingiva is captured between the wedge and the neck portion when the gingiva is in the retracted position. The legs include forward extending surfaces to form a shield between the area of treatment, interproximal gingival tissue, and the laterally adjacent teeth.

6 Claims, 1 Drawing Sheet

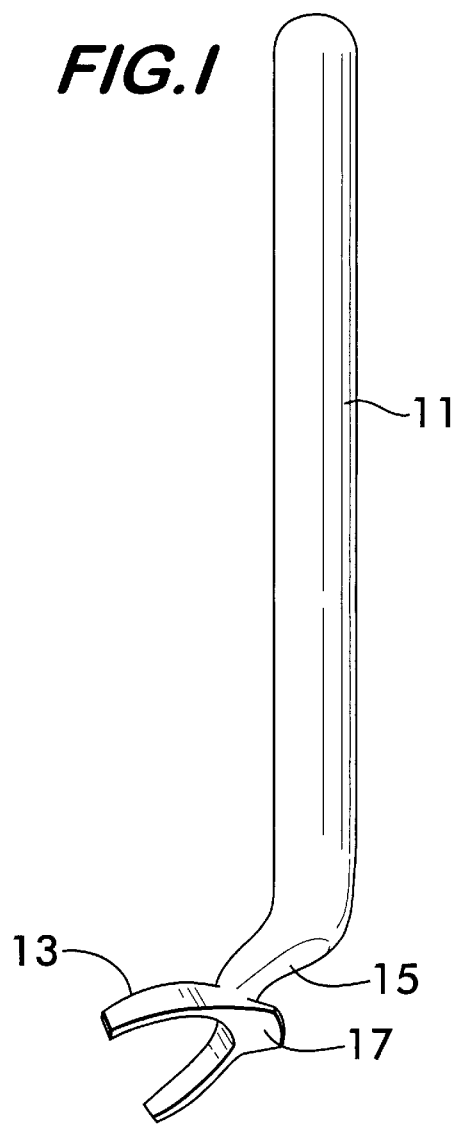
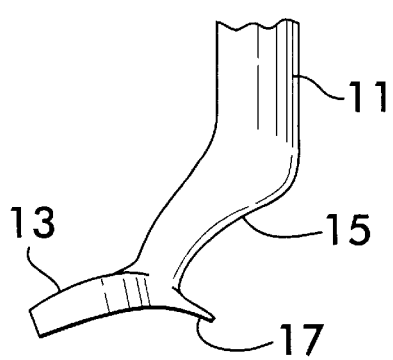
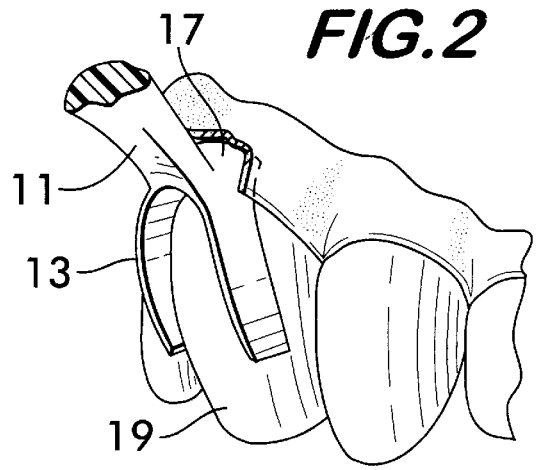
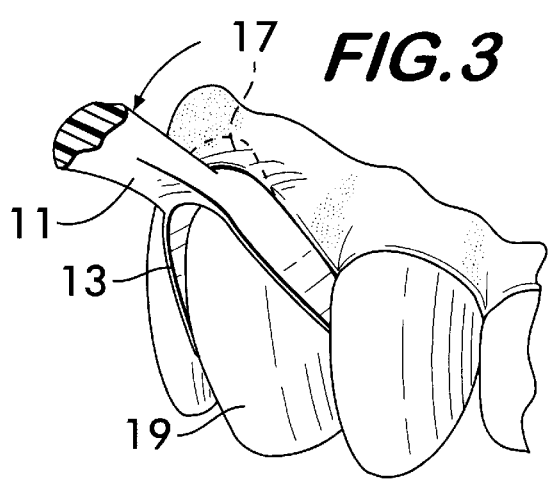
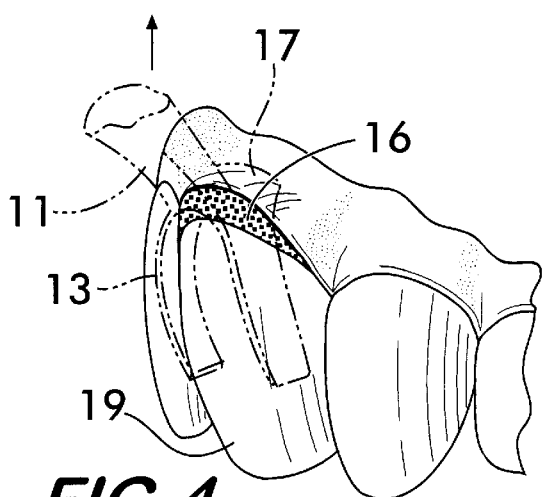

GINGIVAL RETRACTOR

FIELD OF THE INVENTION

The present invention relates to hand-held dental instruments. More specifically it relates to a tool used to assist in the repair of teeth by exposing and isolating the work area of the tooth.

BACKGROUND OF THE INVENTION

In dentistry, it is common practice to employ different techniques such as drilling out the decayed material and replacing it with a restorative, or to otherwise treat teeth using burs, micro etching or acid etching. These practices in dentistry require that a work area of the tooth be exposed and isolated so that it is accessible and that the areas around the tooth are protected from possible harmful effects of the procedure. A type of dental instrument for achieving this desired access and protection are gingival retraction tools, for example as shown in U.S. Pat. No. 4,854,867 entitled "Dental Tools for Facilitating Gingival Retraction" issued on Aug. 8, 1989. As disclosed, this tool facilitates gingival retraction in a way which substantially reduces the irritation, laceration and tearing of the marginal gingiva. The device comprises a working member at the end of the shank which has a curved edge shaped to conform to the curvature of the root surface of the tooth at the gingiva level. It further includes a concaved face terminating at the curved edge. However, a problem with this device and other similar tools is properly locating the tool against the tooth and holding the tool steady during the dental procedure. They have the further disadvantages of size, weight and shape that make them bulky and difficult to use in some areas of the mouth. Also, dental tools of this type must be sterilized after each use.

SUMMARY OF THE INVENTION

In order to solve the problems in the art with gingival retraction tools of the above described type, the present dental tool invention has been devised. The tool is a compact, lightweight, plastic disposable instrument which is convenient and easy to use. Because it is disposable, it does not need to be sterilized. An elongated handle with a horseshoe-shaped guard at the working end is configured to follow the anatomical shape and curvature of the tooth. Because the tool is inexpensive to make in quantity, different sizes and shapes of the tool may be provided to accommodate different sizes and shapes of teeth.

A unique and important aspect of the present invention is a posterior sub-gingival wedge which extends from the backside of the guard. A neck portion of the handle is positioned and shaped so that when retracted, the gingiva is firmly held in the space between the backside surface of the handle neck and the wedge which is inserted under the gingiva. At the same time, the resilience of the gingiva holds the wedge against the tooth. As a result, the wedge provides at least two important functions: first, it facilitates retraction of the gingiva which is firmly held between the wedge and the neck of the tool; and secondly, it provides a point of securement against the root of the tooth which adds to the positional stability of the tool making it easier to center on the tooth and hold it in place.

More specifically, the applicant has invented a dental tool composed of molded plastic for gingival retraction comprising an elongate handle, a horseshoe-shaped guard at an operative end of the handle, the guard including a pair of downward-extending elongate legs, a curved neck portion interconnecting the handle and the guard, and a wedge extending rearwardly from a top portion of the guard such that the legs of the guard lie along the surface of a tooth when the wedge is inserted between the gingiva and the root of the tooth at the gingival margin. The gingiva is captured between the wedge and the neck portion when the gingiva is in a retracted position. The wedge extends from a point approximately in the middle of the legs and includes a concave tip having a curvature substantially matching the curvature of a human tooth. The legs include forward extending surfaces to form a shield between the area of treatment, interproximal gingival tissue, and the laterally adjacent teeth.

Thus, the disadvantages in the art described above have been overcome. Other objects and advantages of the invention will be apparent to those of skill in the art from the following drawings and description of the preferred embodiment of the invention.

BRIEF DESCRIPTION OF THE DRAWINGS

FIG. 1 is a right side bottom isometric view of the invention.

FIG. 1A is a right side elevation view.

FIGS. 2, 3 and 4 are upper right front isometric views of the operational sequence of retracting a person's gingiva utilizing the invention.

DESCRIPTION OF THE PREFERRED EMBODIMENT

Referring now to FIG. 1, the present invention includes an elongated handle 11 having a horseshoe-shaped guard 13 at the operative end thereof The guard includes downward extending legs which have a forward projecting surface. A sub-gingival wedge element 17 projects posteriorly from the top of the guard. An angled neck 15 connects the handle to the guard, and further includes a curved rear surface adjacent the wedge 17. The relationship between the curved rear surface of the neck and the wedge element 17 is more clearly shown with regard to FIG. 1A, with like parts being numbered the same.

Referring now to FIGS. 2, 3 and 4, three basic steps in utilizing the invention are shown. In the first step shown in FIG. 2, the wedge element is inserted under the marginal gingiva. In the next step shown in FIG. 3 the handle is rotated downward in the direction of the arrow using the wedge element as a fulcrum. This places each leg of the horseshoe-shaped guard 13 against and around the sides of the subject tooth 19 which centers the tool on the tooth. The handle is then pulled upward in the direction of the arrow as shown in FIG. 4 which forcefully retracts the gingiva to expose the work area of the tooth 16 that is normally covered by the gingiva in its undisturbed state. When the wedge 17 is driven more deeply under the gingiva against the root of the tooth, as shown in FIG. 4, it will be apparent to those of skill in the art that the tool becomes firmly held against the surface of the tooth by the resilience of the gingiva. This makes it very easy for the dentist to hold the tool at this angle which can only be released from the gingiva by first pushing the tool downward away from the gingiva. In this position, the legs of the guard 13 form lateral barriers having forwardly extending surfaces to shield the adjacent teeth and gingiva from the exposed area 16. The exposed area is now accessible for treatment.

The ease of use of the invention is further provided by the material of its construction which is preferably molded plastic. The use of plastic makes the tool light in weight and extremely inexpensive to manufacture in quantity. This makes it economical to provide a dentist with a variety of different sizes of tools to match the size of the tooth. Its economy also makes it reasonable to use as a disposable product so that sterilization is not needed.

It should be understood that there may be modifications and adaptations to the invention as described which are still within the spirit and scope of the invention which should be defined only by the following claims and their legal equivalents. It will be readily understood, for example, that while the tool has been described in its orientation for use against upper teeth, the orientation may be inverted so that it may be likewise used in conjunction with the treatment of lower teeth.

What is claimed is:

1. A dental tool for gingival retraction and protection, comprising:

an elongate handle;

a horseshoe-shaped guard at an operative end of the handle, said guard including a pair of downward extending elongate legs;

a curved neck portion interconnecting the handle and the guard; and a wedge extending rearwardly from a top portion of said guard such that said legs of said guard lie along the surface of a tooth when the wedge is inserted between the gingiva and the root of the tooth at the gingival margin.

2. The dental tool of claim 1 wherein said gingiva is captured between said wedge and said neck portion when said gingiva is in a retracted position.

3. The dental tool of claim 2 wherein said wedge extends from a point approximately in the middle of said legs.

4. The dental tool of claim 3 wherein said wedge further includes a concave tip having a curvature substantially matching the curvature of a human tooth.

5. The dental tool of claim 4 wherein said tool is composed of molded plastic.

6. The dental tool of claim 1 wherein said legs include forward projecting surfaces.

* * * * *